United States Patent
Garcia et al.

(10) Patent No.: US 8,628,546 B2
(45) Date of Patent: Jan. 14, 2014

(54) SURGICAL INSTRUMENT FOR SUTURING THE SKELETAL MUSCLE SYSTEM AND SURGICAL TECHNIQUE USING SAME

(76) Inventors: Pedro Guillen Garcia, Madrid (ES); Tomas Ramos Marin, Madrid (ES)

( * ) Notice: Subject to any disclaimer, the term of this patent is extended or adjusted under 35 U.S.C. 154(b) by 915 days.

(21) Appl. No.: 12/524,547

(22) PCT Filed: Jan. 16, 2008

(86) PCT No.: PCT/ES2008/070006
§ 371 (c)(1), (2), (4) Date: Mar. 12, 2010

(87) PCT Pub. No.: WO2008/090252
PCT Pub. Date: Jul. 31, 2008

(65) Prior Publication Data
US 2010/0198234 A1 Aug. 5, 2010

(30) Foreign Application Priority Data
Jan. 25, 2007 (ES) .................................. 200700206

(51) Int. Cl.
*A61B 17/04* (2006.01)
(52) U.S. Cl.
USPC .......................................................... 606/144
(58) Field of Classification Search
USPC ........................................ 606/139, 144–150
See application file for complete search history.

(56) References Cited

U.S. PATENT DOCUMENTS

| 5,266,075 | A | 11/1993 | Clark et al. |
|---|---|---|---|
| 5,752,964 | A | 5/1998 | Mericle |
| 5,980,558 | A | 11/1999 | Wiley |
| 6,770,084 | B1 * | 8/2004 | Bain et al. ..................... 606/144 |

FOREIGN PATENT DOCUMENTS

| ES | 2130580 | 12/1995 |
|---|---|---|
| WO | 01/06933 A2 | 2/2001 |

\* cited by examiner

*Primary Examiner* — Gregory Anderson
(74) *Attorney, Agent, or Firm* — Seed IP Law Group PLLC

(57) ABSTRACT

Surgical suture instrument for the muscular-skeletal system and the surgical technique used by same. A surgical suture system includes an instrument providing for the suture of muscular-skeletal system tissues by the use of blades which go from a withdrawn position to a position for the incision of the tissue to be sutured. The blades carry the suture, which is attached to the tissue by the incision of the blades, in response to a drive force aimed longitudinally from back to front, towards the surgical field. The instrument and the surgical technique allow for single or continuous stitching of suture on all tissue types. Its use in bone suture is particularly surprising, making it possible to join bones, implants, grafts, chondrocyte membranes, flaps, tendons, cartilage, etc. The surgical technique for which the surgical suture instrument is used can be applied in open surgery and in arthroscopy.

10 Claims, 4 Drawing Sheets

US 8,628,546 B2

SURGICAL INSTRUMENT FOR SUTURING THE SKELETAL MUSCLE SYSTEM AND SURGICAL TECHNIQUE USING SAME

BACKGROUND

1. Technical Field

This disclosure relates to the biomedicine sector, specifically the field of muscular-skeletal surgery and, within same, the instruments used in open surgery and arthroscopy, specifically for suture with surgical thread, and the techniques used by the invention.

2. Description of the Related Art

Open surgery uses stitching with surgical suture to close wounds caused to the muscular-skeletal system by accidental damage or made during surgical procedures. The concept of stitching includes single stitch sutures and continuous suture with surgical thread, as well as the use of staples. The muscular-skeletal system includes muscles, tendons, cutaneous and subcutaneous tissue, cartilage, etc. However, there is no suturing to bone tissue of implants, of the periosteum type or similar systems which imitate the attributes of the periosteum. Most suture techniques existing at present are based around suture using a needle with surgical thread, requiring suturing to be carried out manually by the surgeon or their assistants.

However, current surgical techniques do not allow for joining muscular-skeletal system tissues using continuous suture with thread or several single stitches, particularly suture involving bone tissue, which cannot be sutured manually using a needle and suture. One of the problems that embodiments of this invention resolves is precisely this, suturing on bone or cartilage, particularly when the suture is arthroscopic. Open surgery using a needle and suture, except in the case of bone, presents no greater problem. However, due to the reduced size of the surgical field, arthroscopic suture using a needle and suture is almost impossible.

BRIEF SUMMARY

The embodiments of the invention consist of a new surgical suture system consisting of an instrument providing for the suture of muscular-skeletal system tissues by the use of blades which go from a withdrawn position to a position for the incision of the tissue to be sutured. The blades carry the suture, which is attached to the tissue by the incision of the blades, thanks to a drive force aimed longitudinally from back to front, towards the surgical field. The instrument and the surgical technique used allow for single or continuous stitching of suture on all tissue types. Its use in bone suture is particularly surprising, making it possible to join bones, implants, grafts, chondrocyte membranes, flaps, tendons, cartilage, etc. The surgical technique for which the invention is used can be applied in open surgery and in arthroscopy.

One application where this instrument and the arthroscopic technique it uses are particularly useful is in membrane/matrix-induced autologous chondrocyte implantation (MACI). This new technique makes it possible to seed a purified collagen membrane with cultivated autologous chondrocytes. The MACI implant is attached with as many stitches as may be necessary depending on its shape, including with continuous suture; after attaching, if any part is left without a good contact, it can be improved with fibrin glue. This procedure can be carried out not only by means of open surgery, but also by arthroscopy or miniarthrotomy.

The embodiments of the invention make the joining, for example, of periosteum flaps or chondrocyte-seeded collagen membranes or matrices, a firm joining during the surgical process, whether open or in arthroscopy or similar techniques, preventing unwanted moving during the operation. Likewise, the join achieved by using the instrument and technique described herein is more lasting, either on its own or in combination with fibrin, preventing subsequent accidental detachments of the implant, which can be an extraordinary complication in the post-operation and rehabilitation of the affected area, generally requiring further surgery to remove the detached implant and install a new one. Thanks to the new suture instrument and the new surgical methods used, described in this application, the sensation of pain in operated patients is reduced significantly, along with infection, delamination, phlebitis, the size of subchondral oedemas, etc., with improvements in all known the secondary effects and complications association with this type of surgery.

DETAILED DESCRIPTION

Figure 1:
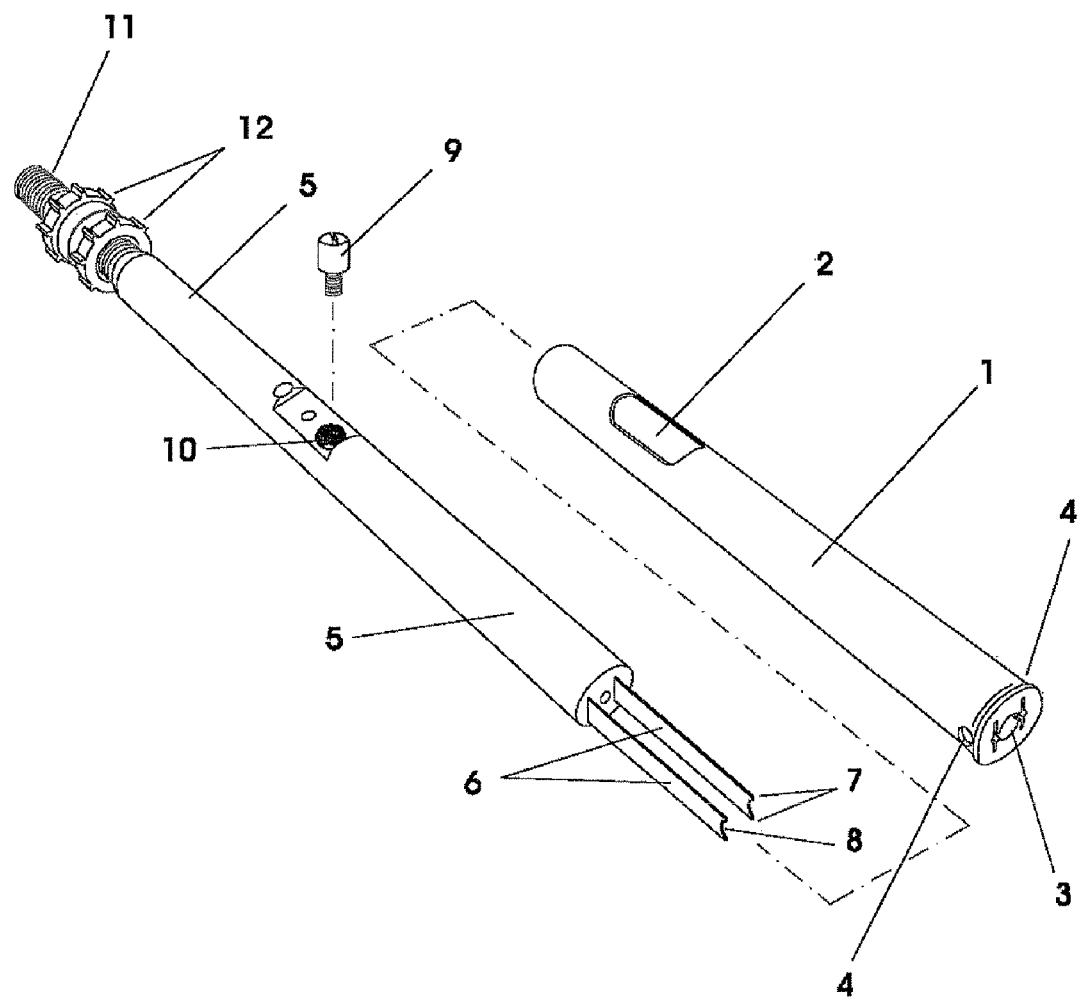
FIG. 1 is a partially exploded isometric view of a suture instrument according to one illustrated embodiment of the invention, the suture instrument including two blades for use in suturing using single stitches with flexible suture or staples.

An embodiment of the invention includes a surgical instrument that consists of an external cylinder (1) containing an internal cylinder (5) holding blades (6) arranged at the end of said external cylinder. The geometrical shape chosen for the external part (1) and internal part (5) is a cylinder, but could equally be any other, such as a prism, for example. The internal cylinder can move lengthways, forwards and backwards, inside the external cylinder. The trajectory of the movement of the internal cylinder inside the external cylinder is limited by a stop (3) which an incision limit and a retraction limit. In a preferred form, the refraction limit consists of a groove (2) in the external cylinder, with a screw (9) threaded into a hollow (10) in the internal cylinder. This screw is higher than the groove in the outside cylinder, so that the internal cylinder, and the blades with it, move between the two ends of the groove, upper and lower, which the screw comes up against. This mechanism may be replaced by any other to limit the length of movement of the internal element inside the external element. This device also stops the internal element rotating inside the external element during retraction, for example, which would leave the blades unaligned with their respective openings in the front end (3) of the external element.

As in the case of the groove (2), any other equivalent mechanism to stop the internal element (5) twisting inside the external element (1) may be used. An equivalent element to that described here to prevent rotation between the external and internal elements could, for example, be a system of complementary guides made on the outside surface of the internal element (5) and in the inside of the external element (1), with the guides coupling complementarily, preventing the elements twisting against each other. The blades are removable, installed inside the internal cylinder, and may be removed when their useful life is over, when they suffer any deformation hindering their correct use, or simply for sterilization. The material of the external and internal cylinders, preferably, is stainless steel. The blades are any steel alloy offering strength and resistance.

At the end opposite the terminal where the suture blades are installed, the internal cylinder has a coupling mechanism, preferably in the form of a threaded part (11), where the hammer mechanism or driving system can be attached, either directly or by a nut system. The driving mechanism for the internal cylinder and, accordingly, the suture blade incision, can be operated mechanically by the surgeon by means of small taps, preferably assisted by a hammer system. However, this driving system may also be any described in the state of the art, including, among others, ultrasonic, hydraulic, electrically or electromagnetically operated, and even computer controlled.

The suture is threaded through a hole (4) parallel to the sides of the front end (3) of the external cylinder, which also acts as the front stop for the internal blade-holding cylinder. This end (3) also has in its middle a hole to hold and guide the suture pulled by the blade or blades, in addition to two grooves, which keep the blades in their puncture position. To thread the suture, the internal cylinder is pulled back. The front end-stop (3) of the external cylinder has respective openings with the same profile as the blades, to guide them perfectly in any position of the cylinders, and so that only the blades can extend to the outside. When the driving mechanism hits against the back of the internal cylinder with a certain level of force, the cylinder is moved forwards, taking the threaded suture with it. For this, the blades have a profile with two sharper cutting edges (7) and a furrow (8) between the two cutting edges. This is what drags the suture, and it is not sharpened, so as not to cut the suture. The two cutting edges of each blade penetrate the tissue, thanks to the impulse hitting against the back of the internal cylinder, sewing the suture to the tissue. The force to be exercised against the internal cylinder must be proportional to the resistance to incision of the tissue being operated—greater for hard tissue (bone, tendon, cartilage, etc.), less for softer tissues (muscle, subcutaneous, etc.).

The suture instrument also has a mechanism to regulate the blade incision depth, depending on the tissue to be sutured and the thickness of the suture being used. In a preferred embodiment of this invention, this mechanism regulating the blade incision depth consists of at least two nuts (12) screwed on in opposite directions, so that they cannot move on the back end (11) of the internal element (5). These nuts act as a stop against the internal element (1) regulating the forward movement of the internal element (5) and, accordingly, how far the blades extend outside, directly proportional to the incision depth for the suture. At the same time, the regulating mechanism leaves sufficient space at the front end (3) of in accordance with the thickness of the suture. This embodiment of the invention should not be considered any limit on its scope. Any other regulating mechanism equivalent to the nuts (12) can be used to limit how far the blades extend out and, accordingly, the depth of the incision to be made. For example, instead of the nuts, a mechanism in which the parts used to attach the propulsion system, depending on where it is screwed on, could act as a stop against the external element (1).

There are two preferred embodiments of implementing the inventive method, i.e., continuous stitching with elastic suture in different thicknesses, and single stitching, also with elastic suture of different thicknesses or elastic staples. In the former case, a single blade in the center of the movable internal element (cylinder) is used. In the variant with separate stitches or staples, instead of a single blade at least two parallel blades are used, equidistant from the respective ends of the movable internal element (cylinder). The blades, especially in the 2 or more variant, can be in different shapes. Optionally, for example, they may have grooves in their outside edge, to guide the suture or staple during suturing.

We now describe the use of the above described instrument in the two main surgical method variants to which it may be applied, as an example of, but not limited to, the possible uses and applications of the invention.

1) Open Technique 4-6 fragments of cartilage the size of a grain of rice are extracted via arthroscopy from a non weight-bearing area of the ipsilateral knee (200-300 mg of healthy cartilage). The chondrocytes are cultivated and expanded and then applied in an absorbent I/III purified porcine collagen lamicoid membrane. The lamicoid structure has a smooth side which acts as a natural barrier and is put against the joint, and a porous side, put against the bone. The chondrocytes are seeded on the porous side of the membrane in a type of three-dimensional matrix. The membrane is tear resistant and can be cut to the desired shape. The membrane is not antigenic (the immunogenic telopeptides are eliminated during the manufacture process); it is bioabsorbent.

An incision is made in the knee area with a scalpel or similar instrument. After miniarthrotomy or open incision, the cartilage defect is scraped to eliminate the layer of calcified cartilage. A border of stable cartilage with strong vertical walls of healthy cartilage is formed, a template of the chondral defect is taken and the MACI membrane is cut to the right shape using scissors.

The membrane is then fixed in place with the above described suture instrument, with separate stitches or continuous stitches using flexible thread. When suturing with single stitches, in the variant with two blades, the suture or staple for a single stitch is placed in the end of the suture instrument, and the suture operation is repeated by impacting on the back of the internal cylinder of the suture instrument as often as the number of stitches to be given to the membrane to join it to the cartilage. In the continuous suture variant, instead of using bits of suture of the approximate length of one stitch, the suture instrument is threaded with a length proportional to the desired perimeter or suture line and it is stitched with successive impacts, withdrawing the internal cylinder with, in this case, its one blade, between each impact. In any case, if more homogenous contact is required, fibrin glue (Tissucol, Baxter) can be used.

2) Arthroscopic Technique

Figure 4:
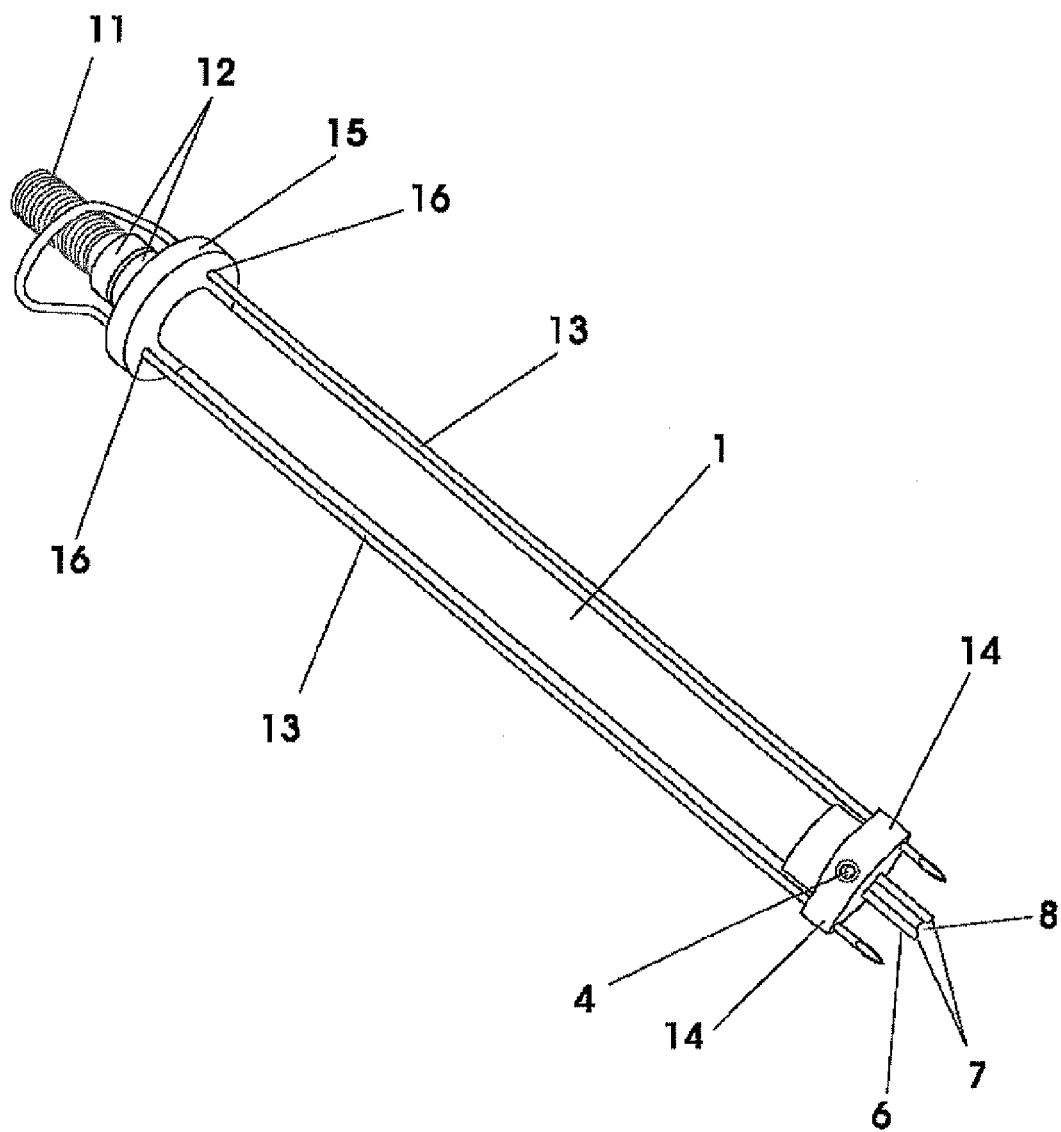
FIG. 4 is an isometric view of a suture instrument according to another illustrated embodiment of the invention, the suture instrument including one blade and a number of needles for use in suturing.

After biopsy and cultivation of the chondrocytes, a conventional arthroscopy is carried out, using a specially-designed arthroscopic cannula, and the cartilage defect is scraped, using a ring-shaped curette, to eliminate the layer of calcified cartilage. A border of stable cartilage with strong vertical walls of healthy cartilage is formed. The size of the lesion is calculated using a specially designed gauge and a flexible ruler. A template is taken and put against the cartilage defect to check the size, and then the membrane is cut to the right size. When the implant is prepared, the instrument, in the form of a preferred embodiment of the invention, has two needles that bring the membrane to its position. At this time, the impulse that causes the withdrawal of the needles is started, allowing for entry of the blades that fix the membrane to the area previously prepared. Next the required number of stitches is made, and finally, as the case may be, fibrin glue is used. This preferred form of the invention is illustrated in FIG. 4, in which the membrane (or flap) is placed on deteriorated cartilage, joined to the suture instrument by at least one needle and preferably two needles (13) arranged parallel to the external element (1) and attached to it by the respective sockets (14, 15) arranged, respectively, at the front and back of the external element (1) in which respective holes (16) have been made to insert the needles holding the chondrocyte membrane.

The embodiments of this invention offer viable treatment for large and deep osteochondral and chondral defects, affecting the thickness of the knee and ankle in young and middle-aged patients. With the instrument and suture method proposed in this application, the MACI procedure is a simple procedure and may be carried out via arthroscopy or miniarthrotomy, allowing for implants in places where it would be difficult or impossible to suture a periosteum patch. This new suture instrument makes surgical implantation of autologous chondrocytes via arthroscopy a relatively simple procedure, avoiding many of the secondary post-operation complication of operated patients.

FIG. 1 shows a dismantling of the suture instrument in its 2-blade variation, for single stitches with flexible suture or staples. The suture instrument includes, the following elements, identified by reference numeral:

(1) Fixed cylindrical external element.
(2) Groove or opening that limits the movement and twisting of the internal cylindrical element (5) inside the external cylinder.
(3) Front end of the fixed external cylindrical element that acts as a stop for incision or for the inwards movement of the internal element. It has openings for 2 parallel blades and a central hole for the suture pulled by the blade(s).
(4) Lateral holes at the end of the external cylinder, for insertion of the suture thread or staple.
(5) Movable internal element, preferably cylindrical.
(6) Incision blades.
(7) Cutting edges of the blades.
(8) Groove between the cutting edges where the suture thread or staple is placed.
(9) Screw that acts as a stop on the movement of the internal element when it comes up against the ends of opening 2.
(10) Grooved housing made in a thin end of the internal movable element for the screw acting as a stop.
(11) Element for screw attachment of the hammer element.
(12) Nuts used to regulate the depth of the incision of the blades.

Figure 2:
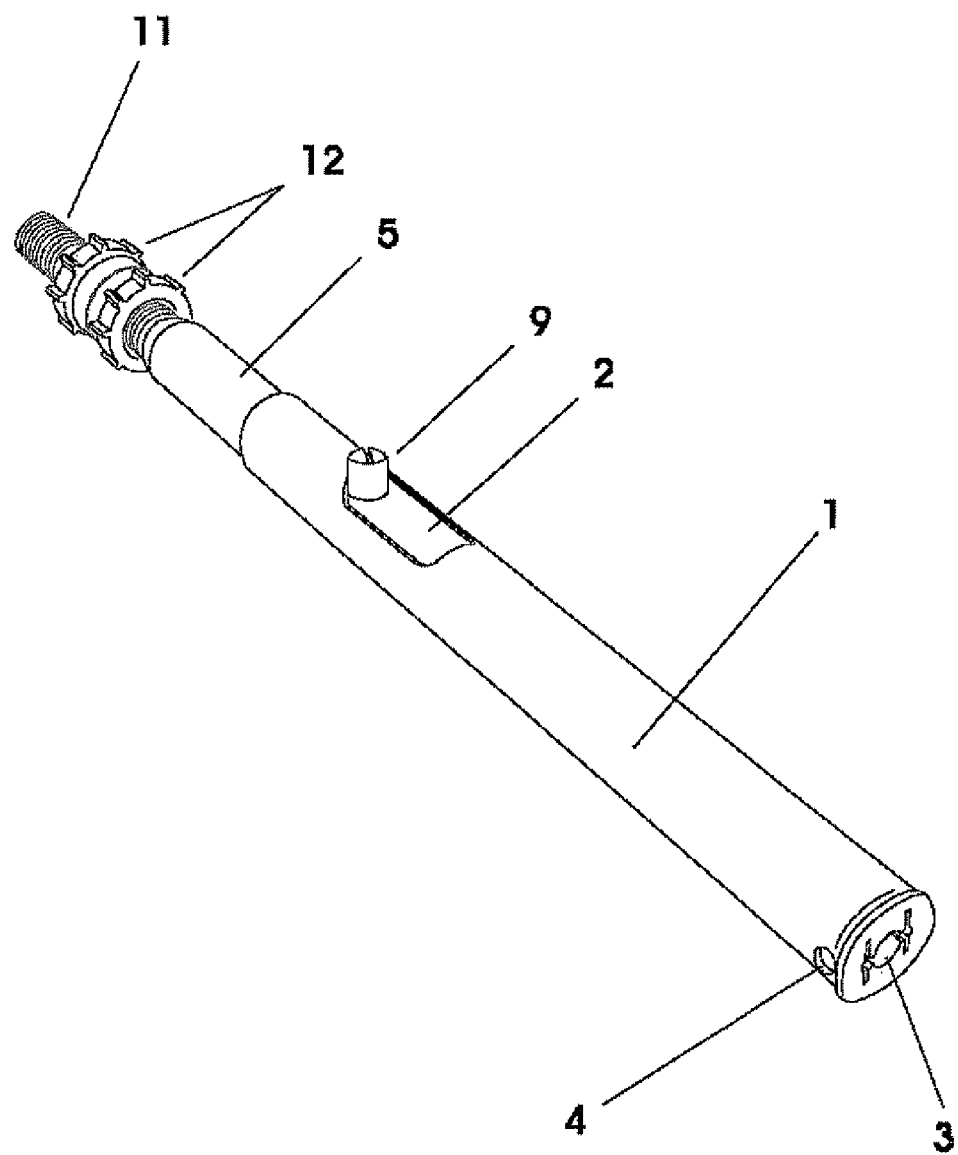
FIG. 2 is an isometric view of the suture instrument of FIG. 1 showing an external cylinder and an internal cylinder located inside the external cylinder in a withdrawn position such that the blades are withdrawn.

FIG. 2 shows the suture instrument of FIG. 1 with the internal cylinder (5) inside the external cylinder (1), in withdrawn position, in which the blades (6) are withdrawn.

Figure 3:
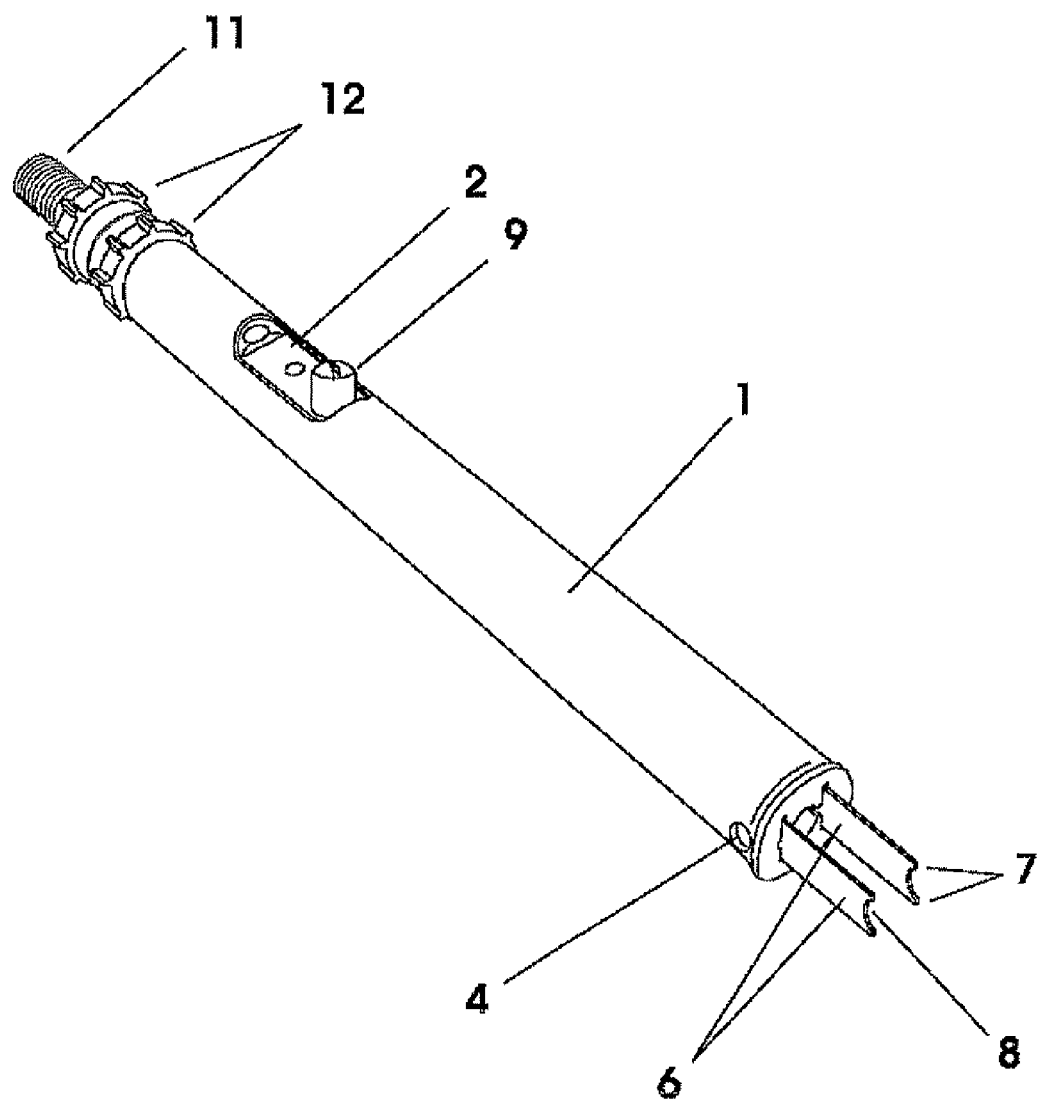
FIG. 3 is an isometric view of the suture instrument of FIG. 1 showing the internal cylinder in a forward or incision position, such that the blades extend from the external cylinder.

FIG. 3 shows the suture instrument of FIG. 1 with the internal cylinder (5) inside the external cylinder (1), in forward (incision) position, exposing the blades (6).

FIG. 4 shows a variant of the suture element with membrane carrying needles (13) attached to the external element (1) by sockets (14, 15) at the front and back end of the external element (1). These sockets have holes (16) the same size as the needles (13) and are used to guide them.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A surgical suture method for the muscular-skeletal system employing a surgical suture instrument having an external element; an internal element received in the external element for lengthways movement inside the external element; and at least one blade carried by the internal element, the at least one blade positioned proximate a proximate end of the surgical suture instrument which is closest to a tissue during use of the surgical suture instrument, the external element having two holes through which a suture material extends, and the blades having at least two sharp cutting edges and an unsharpened groove between the cutting edges to receive a portion of the suture material, the surgical suture method comprising:
    positioning the proximate end of the surgical suture instrument adjacent tissue to be sutured; and
    moving the internal element to extend the at least one blade along with the suture material carried by the unsharpened groove out of the external element to physically engage the tissue with the suture material on a forward pass of the at least one blade in a direction in which the at least one blade cuts the tissue.

2. The surgical suture method according to claim 1, further comprising:
    repeatedly moving the internal element to extend the at least one blade from the external element to physically engage the tissue with the suture material to form a continuous multi-stitch suture.

3. The surgical suture method according to claim 1 wherein the moving of the internal element forms a single stitch suture.

4. The surgical suture method according to claim 1 wherein positioning the proximate end of the surgical suture instrument adjacent tissue to be sutured includes positioning the proximate end of the surgical suture instrument adjacent an open wound in the tissue.

5. The surgical suture method according to claim 1 wherein positioning the proximate end of the surgical suture instrument adjacent tissue to be sutured includes positioning the proximate end of the surgical suture instrument via an arthroscope.

6. The surgical suture method according to claim 1 wherein positioning the proximate end of the surgical suture instrument adjacent tissue to be sutured includes positioning the proximate end of the surgical suture instrument adjacent at least one of bone tissue, cartilage, periosteum flaps, collagen membranes, matrices impregnated with chondrocytes, tendons or ligaments.

7. The surgical suture method according to claim 1, wherein the tissue to be sutured includes bone tissue, the method further comprising:
    applying a layer of fibrin glue between a collagen membrane or matrix and the bone tissue.

8. The surgical suture method according to claim 1, further comprising:

adjusting a stop to set an amount of travel of the internal element with respect to the external element to limit a distance by which the at least one blade may extend from the external element.

9. The surgical suture method according to claim 1, further comprising:

repeatedly driving the internal element with respect to the external element via a hammer or driving mechanism.

10. The surgical suture method according to claim 1, further comprising:

engaging a portion of the tissue with at least one needle that extends from a socket located at the proximate end of the surgical suture instrument.

* * * * *